(12) United States Patent
Friedman et al.

(10) Patent No.: US 7,074,392 B1
(45) Date of Patent: Jul. 11, 2006

(54) CONTROLLLED DELIVERY SYSTEM OF ANTIFUNGAL AND KERATOLYTIC AGENTS FOR LOCAL TREATMENT OF FUNGAL INFECTIONS

(75) Inventors: Michael Friedman, Jerusalem (IL); Daniella Licht, Givat Shmuel (IL); Rachel Cohen, Hadera (IL); Avraham Yacobi, Englewood, NJ (US)

(73) Assignee: Taro Pharmaceutical Industries Limited, Haifa Bay (IL)

( * ) Notice: Subject to any disclaimer, the term of this patent is extended or adjusted under 35 U.S.C. 154(b) by 0 days.

(21) Appl. No.: 09/534,960

(22) Filed: Mar. 27, 2000

(51) Int. Cl.
A61K 6/00 (2006.01)
A61K 7/00 (2006.01)
A61K 7/04 (2006.01)
A01N 25/34 (2006.01)

(52) U.S. Cl. .................... 424/61; 424/401; 424/404
(58) Field of Classification Search ............... 424/61, 424/401, 404
See application file for complete search history.

(56) References Cited

U.S. PATENT DOCUMENTS

| | | | |
|---|---|---|---|
| 4,250,164 A | 2/1981 | Bernstein ............... 424/61 |
| 4,402,935 A | 9/1983 | Gordon et al. |
| 4,957,730 A | 9/1990 | Bohn et al. |
| 5,023,082 A | 6/1991 | Friedman et al. |
| 5,160,737 A * | 11/1992 | Friedman et al. ........... 424/401 |
| 5,264,206 A * | 11/1993 | Bohn et al. ............... 424/61 |
| 5,346,692 A | 9/1994 | Wohlrab et al. ........... 424/61 |
| 5,464,610 A | 11/1995 | Hayes, Jr. et al. ........... 424/61 |
| 5,487,776 A * | 1/1996 | Nimni ................. 106/18.35 |
| 5,639,795 A | 6/1997 | Friedman et al. |
| 5,681,849 A | 10/1997 | Richter et al. |
| 5,696,164 A | 12/1997 | Sun et al. |
| 5,856,355 A | 1/1999 | Richter et al. |
| 5,863,527 A * | 1/1999 | Hutchins et al. ........ 424/70.16 |
| 5,968,986 A | 10/1999 | Dyer |
| 6,005,001 A | 12/1999 | Richter et al. |
| 6,007,798 A | 12/1999 | Bohn et al. |
| 6,042,845 A | 3/2000 | Sun et al. |
| 6,075,056 A | 6/2000 | Quigley, Jr. et al. |
| 6,121,314 A | 9/2000 | Richter et al. |
| 6,224,887 B1 | 5/2001 | Samour et al. ........... 424/401 |
| 6,231,875 B1 | 5/2001 | Sun et al. .............. 424/401 |
| 6,391,879 B1 | 5/2002 | Reeves |
| 2002/0168404 A1 | 11/2002 | Rault et al. |

FOREIGN PATENT DOCUMENTS

| | | |
|---|---|---|
| EP | 0 440 298 A1 | 8/1991 |
| GB | 2 202 743 A1 | 10/1988 |
| WO | WO 99/39680 A1 | 8/1999 |
| WO | 0 974 365 A1 | 1/2000 |

* cited by examiner

Primary Examiner—Thurman K. Page
Assistant Examiner—Sharon Howard

(57) ABSTRACT

A topical sustained release delivery system for delivery of antifungal agents to the finger or toenails achieving high penetration through the nails by combining the antifingal agent with a keratolytic agent and a humectant. The pharmaceutical sustained release topical preparation is provided in a varnish or spray form for treating the nail and surrounding tissues, where the active ingredient is an antifungal agent, a keratolytic agent, or preferably a combination of an antifuingal and a keratolytic agent. The composition may further comprise an antibacterial, an antiviral, an antipsoriatic agents, or combinations thereof.

39 Claims, No Drawings

CONTROLLLED DELIVERY SYSTEM OF ANTIFUNGAL AND KERATOLYTIC AGENTS FOR LOCAL TREATMENT OF FUNGAL INFECTIONS

FIELD OF THE INVENTION

The present invention relates to a sustained release composition in the form of varnish or spray comprising an antifungal agent, a keratolytic agent, or preferably a combination of antifingal and keratolytic agents, for local treatment of fungal infections of the nails and/or surrounding tissues. The composition additionally features a humectant, water, one or more film-forming polymers, and solvents. The composition may further comprise an antibacterial agent, an antiviral agent, an antipsoriatic agent or a combination thereof.

BACKGROUND OF THE INVENTION

Fungal infections are probably the most common disorder of nails encountered in medical practice. It has been estimated that approximately 90% of elderly people have some degree of toenail involvement with fungi. Conditions of moisture and occlusion of the lower extremities favor fungal colonization. Pain may result from extreme deformity of the nail plate, but usually, the complaint is one of cosmetic appearance. The most common organisms involved in the fungal infections of the nail are *Trichophyton rubrum, Trichophyton mentagrophytes, Epidermophyton floccosum, Candida albicans, Microsporum persiccolor*, Cephalosporium species, Aspergillus species, and *Fusarium oxysporum.*

Fingernail infection is of far greater importance cosmetically and fortunately clears faster than toenail infection because of the more rapid growth rate of fingernails. Despite this, 4–6 months of oral griseofulvin may be required to bring about complete clearing of the fingernail. For toenail infections with extensive involvement of multiple digits, withholding treatment may be the best decision. One of the factors in the treatment decision is whether the patient is taking other medications, as griseoftilvin interacts with several drugs, including anticoagulants.

Griseofulvin was the drug of choice for many years, but its low cure rate and the development of newer, more effective drugs has caused it to lose favor. Current therapeutic alternatives include itraconazole and terbinafine. These drugs are well tolerated, but attention to drug interactions is still necessary [Trepanier, E. F and Amsden, G. W. *Annals of Pharmacotherapy*, 32, 1998, 204–214].

At present, topical treatment of fungal infections directly to the nail plate is discouraging. Creams or solutions containing antifungal agents, such as imidazole derivatives, are able to deliver the active agent to the nail only for a short period of time and their permeability/penetration through the nail is very low.

U.S. Pat. No. 5,120,530 discloses an antimycotically-active nail varnish, containing an antimycotically-active substance (a morpholine derivative) and a water-insoluble film former which is a copolymerizate of acrylic acid esters and methacrylic acid esters having a low content of quaternary ammonium groups. The formulations disclosed are expected to be poorly effective because they do not contain a keratolytic agent or a humectant. As a result, the nail permeability and consequently the penetration of the antimycotic agent will be very low. In the present invention the humectant entraps the water in the film after evaporation of the organic solvents, thus enabling the solubilization of the active agents in the film. Because the water content of the nail is very low, the presence of water in the film should hydrate the nail and improve the transport of the active agents into the nail. The keratolytic agent should also help by increasing the penetration of the antifungal agent into the deeper layers of the nail.

U.S. Pat. No. 4,957,730 discloses a nail varnish comprising a water-insoluble film-forming substance and an antimycotic substance, specifically 1-hydroxy-2-pyridones. The formulations disclosed do not contain a humectant. The nail permeability of the formulations disclosed and consequently the penetration of the active agent into the deeper layers of the nail is expected to be very low, thereby failing to achieve the desired pharmacological action and cure.

U.S. Pat. No. 5,814,305 discloses a nail preparation comprising an antifungal agent, at least one hydrophilic penetration agent, and a water-alcohol solvent medium. The formulations disclosed are disadvantageous; they are in the form of a lotion or fluid gel and do not contain a film-forming agent. As a result a sustained release action is not achieved with these formulations. The formulations disclosed are disadvantageous since such a dosage form would require multiple applications of the formulation, leading to poor patient compliance. Because of the hydrophilic character of the formulations, in the presence of water or mechanical contact, the lotion or gel will likely be washed off or removed from the nail, thereby reducing the accumulation of the active agents in the nail.

UK Patent Appl. No GB2202743 A discloses a topical antifungal composition in the form of a lotion, gel or varnish, comprising at least 1% by weight (relative to the total weight of the composition) of miconazole nitrate or econazole nitrate dissolved in a mixture of water, urea, and a water-soluble dissolving intermediary. Urea is used in the formulation as a solubility increasing agent. When the composition is in the form of a varnish it contains a resin. The lotion and gel formulations disclosed are disadvantageous since such a dosage form will not provide sustained release action and would require multiple applications of the formulation, leading to poor patient compliance. Because of the hydrophilic properties of the formulations, in the presence of water or mechanical contact, the lotion or gel will likely be washed off or removed from the nail, thereby reducing the accumulation of the active agents in the nail. The varnish formulations disclosed are disadvantageous, and do not contain a humectant. As a result, the antifungal agent will not be solubilized in the film, and the hydration of the nail and transport of the antifungal agent through the nail will be very low, preventing achievement of the desired pharmacological action. In addition, UK Patent Appl. No GB2202743 A describes a delivery system specific for miconazole nitrate or econazole nitrate, which is not therefore a general delivery system for other antifungal agents.

None of these prior art references suggest or disclose the use of a combination of antifungal agent, keratolytic agent, and a humectant (glycerol at high concentrations). This combination is particularly advantageous because it increases the penetration of the active antifungal agent through the nail and thus provides better pharmacological action.

U.S. Pat. No. 5,346,692 discloses a nail lacquer for treating onychomycosis, which comprises (a) a film former agent, (b) at least one antimycotically active substance, (c) urea; and (d) a solvent which comprises (i) 50–70 wt. % of acetone; and (ii) 30–50 wt. % of 90 volume % aqueous ethanol. The formulations disclosed are disadvantageous since they use high concentrations of the antimycotically active substance and urea, thereby causing unwanted adverse effects (for example irritation and burning) which leads to poor compliance.

The formulations disclosed do not contain glycerol which would entrap the water in the film after evaporation of the organic solvents. The presence of water in the film enables the active agents to be maintained in a soluble form that is readily available for pharmacological action. Since the water content in the nail is very low, the presence of water in the film hydrates the nail so that the active agents can be delivered into deeper layers of the nail.

There is thus a need for, and it would be useful to have, a better formulation, containing low concentrations of the antifungal and keratolytic agents, to deliver pharmacologically active agents to the nail for the treatment of fungal infection thereof. This formulation would feature a film-forming agent and a humectant preferably glycerol, for trapping water in the film formed on the nail, and the water so trapped would hydrate the nail for delivery of the agent thereto.

This formulation would be lower in cost because of the lower concentrations of the antifungal and keratolytic agents. Additionally, such formulation would reduce the unwanted side effects caused by high concentrations of the antifungal and keratolytic agents and yet be suitable for treatment of fungal infections of the nail and surrounding tissues.

SUMMARY OF THE INVENTION

The present invention provides a pharmaceutical sustained release preparation in a varnish or spray form for local treatment of the nail and surrounding tissues, where the active ingredient is an antifungal agent, a keratolytic agent, or preferably a combination of an antifungal and a keratolytic agent. The composition may further comprise an antibacterial, an antiviral, an antipsoriatic agent or combinations thereof.

In a first embodiment the present invention provides a sustained release nail varnish composition comprising:
 (a) a pharmaceutically effective agent;
 (b) a humectant;
 (c) water;
 (d) less than about 7.5% (w/w) based on the total weight of the composition, of a polymeric film-forming agent;
 (e) at least one additional excipient; and
 (f) a solvent system including at least one volatile solvent.

In a second embodiment the present invention provides a sustained release nail varnish composition comprising:
 (a) an antifungal agent;
 (b) a keratolytic agent;
 (c) a humectant;
 (d) water;
 (e) a polymeric film-forming agent;
 (f) at least one additional excipient; and
 (g) a solvent system including at least one volatile solvent.

In a preferred embodiment the pharmaceutically effective agent is selected from the group consisting of an antifungal agent, a keratolytic agent, and mixtures thereof.

In a preferred embodiment the antifungal agent is selected from the group consisting of amphothericin B, butefanine, butoconazole, carbol-fuchsin, ciclopirox, clioquinol, clotrimazole, econazole, gentian violet, ketoconazole, miconazole, naftifine, nystatin, oxiconazole, sodium thiosulfate, terbinafine, terconazole, tolnaftate, undecylenic acid, therapeutically acceptable salts thereof, derivatives thereof, and mixtures thereof.

In a preferred embodiment the concentration of the antifungal agent in the varnish solution is less than about 1% (w/w).

In a preferred embodiment the antifungal agent is present in concentration of less than about 5% (w/w) based on the weight of the non-volatile components.

In a preferred embodiment the keratolytic agent is selected from the group consisting of urea, sulfur, salicylic acid, podophyllum resin, and mixtures thereof.

In a preferred embodiment the concentration of the keratolytic agent in the varnish solution is less than about 1% (w/w).

In a preferred embodiment the keratolytic agent is present in concentration of from about 0.05% to about 5% (w/w), based on the weight of the non-volatile components.

In a preferred embodiment the pharmaceutically effective agent further comprises an antibacterial, an antiviral, an antipsoriatic agent, or mixtures thereof.

In a preferred embodiment the antibacterial agent is selected from the group consisting of bacitracin, clindamycin, erythromycin, gentamicin, mupirocin, neomycin, tetracyclines, polymyxin B, benzalkonium chloride, boric acid, hexachlorophene, iodine, iodoquinol, mafenide, mercury ammoniated, metronidazole, nitrofurazone, selenium sulfide, silver sulfadiazine, salts thereof, derivatives thereof, and mixtures thereof.

In a preferred embodiment the concentration of the antibacterial agent in the varnish solution is from about 0.01% to about 1% (w/w).

In a preferred embodiment the antibacterial agent is present in concentration of from about 0.05% to about 5% (w/w), based on the weight of the non-volatile components.

In a preferred embodiment the antiviral agent is selected from the group consisting of acyclovir, amantadine, cidofovir, famciclovir, foscarnet, ganciclovir, palivizumab, penciclovir, ribavirin, rimantadine, valcyclovir, salts thereof, derivatives thereof, and mixtures thereof.

In a preferred embodiment the concentration of the antiviral agent in the varnish solution is from about 0.08% to about 0.8% (w/w).

In a preferred embodiment the antiviral agent is present in concentration of from about 0.8% to about 8% (w/w), based on the weight of the non-volatile components.

In a preferred embodiment the antipsoriatic agent is selected from the group consisting of alclometasone, ameinonide, betamethasone, clobetasol, clocortolone, desonide, desoximetasone, diflorasone, fluocinolone, fluocinonide, flurandrenolide, halcinonide, hydrocortisone, mometasone, prednicarbate and triamcinolone, salts thereof, derivatives thereof, and mixtures thereof.

In a preferred embodiment the concentration of the antipsoriatic agent in the varnish solution is from about 0.02% to about 2% (w/w).

In a preferred embodiment the antipsoriatic agent is present in concentration of from about 0.1% to about 10% (w/w), based on the weight of the non-volatile components.

In a preferred embodiment the humectant is selected from the group consisting of glycerol, sorbitol, and mixtures thereof.

In a preferred embodiment the concentration of the humectant in the varnish solution is from about 3% to about 15% (w/w).

In a preferred embodiment the humectant is present in concentration of from about 5% to about 35% (w/w), based on the weight of the non-volatile components.

In a preferred embodiment the water concentration in the varnish solution is less than about 5% (w/w).

In a preferred embodiment the concentration of the water in the film is from about 0.4% to about 25% (w/w).

In a preferred embodiment the polymeric film-forming agent is selected from the group consisting of hydrophobic (water insoluble) polymers.

In a preferred embodiment the hydrophobic (water insoluble) polymer is selected from the group consisting of hydrophobic cellulose derivatives, hydrophobic methacrylic polymers, cellulose acetate phthalate, shellac, derivatives thereof, and mixtures thereof.

In a preferred embodiment the hydrophobic cellulose derivative is selected from the group consisting of ethyl cellulose of any acceptable molecular weight.

In a preferred embodiment the hydrophobic methacrylic polymer is selected from the group consisting of methacrylic acid copolymer type B (USP/NF), methacrylic acid copolymer type C (USP/NF), ammonio methacrylate copolymer type B (USP/NF) and ammonio methacrylate copolymer type A (USP/NF), derivatives thereof, and mixtures thereof In a preferred embodiment the hydrophobic methacrylic polymer is selected from the group consisting of Eudragit S, Eudragit L, Eudragit RS, and Eudragit RL manufactured by Rohm Pharma, but hydrophobic methacrylic polymers from other sources can also be used.

In a preferred embodiment the concentration of the polymeric film-forming agent in the varnish solution is less than about 7.5% (w/w).

In a preferred embodiment the polymeric film-forming agent is present in concentration of from about 8% to about 35% (w/w), based on the weight of the non-volatile components.

In a preferred embodiment the weight ratio of polymer to the antifungal agent is in the range from about 1:0.01 to about 1:0.3.

In a preferred embodiment the weight ratio of polymer to the keratolytic agent is in the range from about 1:0.01 to about 1:1.

In a preferred embodiment the weight ratio of polymer to antibacterial agent is in the range from about 1:0.01 to about 1:0.3.

In a preferred embodiment the weight ratio of polymer to antiviral agent is in the range from about 1:0.02 to about 1:0.2.

In a preferred embodiment the weight ratio of polymer to antipsoriatic agent is in the range from about 1:0.006 to about 1:0.15.

In a preferred embodiment the at least one additional excipient is selected from a group consisting of plasticizers.

In a preferred embodiment the plasticizer is selected from the group consisting of dibutyl sebacate, diethyl phthalate, lanolin alcohols, mineral oil, petrolatum, polyethylene glycol, propylene glycol, triacetin, triethyl citrate, and mixtures thereof.

In a preferred embodiment the concentration of the plasticizer in the varnish solution is from about 0.1% to about 2% (w/w).

In a preferred embodiment the plasticizer is present in concentration of from about 0.5% to about 10% (w/w), based on the weight of the non-volatile components.

In a preferred embodiment the weight ratio of the plasticizer to the polymer is in the range from about 0.04:1 to about 0.3:1.

In a preferred embodiment the volatile solvent is selected from the group consisting of an alcohol, a ketone, and mixtures thereof.

In a preferred embodiment the alcohol is selected from the group consisting of ethanol, isopropyl alcohol, methanol and mixtures thereof.

In a preferred embodiment the ketone is acetone.

In a preferred embodiment the volatile solvent is a mixture of acetone and isopropyl alcohol.

In a preferred embodiment the volatile solvent is present in an amount of is from about 60% to about 90% (w/w), relative to the total weight of the composition.

In a preferred embodiment the volumetric ratio of acetone to isopropyl alcohol is in the range from about 1:4 to about 4:1.

In a preferred embodiment the solvent system further includes at least one non-volatile solvent selected from the group consisting of benzyl alcohol, benzyl benzoate, corn oil, cottonseed oil, ethyl oleate, glycerin, glycofural, isopropyl myristate, isopropyl palmitate, mineral oil, peanut oil, polyethylene glycol, propylene glycol, propylene carbonate, sesame oil, soybean oil, water, and mixtures thereof.

In a preferred embodiment the composition may further comprise preservatives, antioxidants, surfactants and coloring agents.

In a third embodiment the present invention provides a method of preparing a sustained release varnish or spray formulation for treating the nail and surrounding tissues, comprising the steps of (a) preparing a solution including at least one volatile solvent; (b) adding water to the solution prepared in (a); (c) dissolving the pharmaceutically effective agents, and excipients in the solution prepared in (b); (d) adding the humectant to the solution prepared in (c) when the formulation ingredients are completely Is dissolved; and (e) dissolving the polymeric film-forming agents in the solution prepared in (d).

Definitions

By "varnish solution" is meant the total composition before evaporation of the volatile components.

By "film" is meant the non-volatile components, which are remained after evaporation of the volatile components of the varnish solution.

By "concentration or amount relative to the total weight of the composition" is meant concentration in the varnish solution, before application to the nail or before evaporation of the volatile components.

By "concentration or amount based on the weight of the non-volatile components" is meant concentration based on the weight of the components remaining after evaporation of the volatile components (i.e. concentration in the film).

DESCRIPTION OF THE PREFERRED EMBODIMENTS

The aim of this invention was to develop a sustained release delivery system for antifungal agents achieving high penetration through the nail by combining the antifungal agent with a keratolytic agent and a humectant.

The present invention provides a topical, sustained release pharmaceutical preparation in a varnish or spray form for treating the nail and surrounding tissues, where the active ingredient is an anti-fungal agent, a keratolytic agent, or preferably a combination of an antifungal and a keratolytic agent. The composition may further comprise an antibacterial, an antiviral, an antipsoriatic agent or combinations thereof.

The composition features an effective quantity of at least one antifungal agent, an effective quantity of at least one keratolytic agent, a humectant, water, polymers, optionally at least one additional pharmaceutical excipient and finally a solvent medium. The additional excipients include plasticizers. The composition may further comprise an effective quantity of at least one antibacterial, antiviral, antipsoriatic agent or combinations thereof.

The delivery system is in the form of a solution or spray for self-application by the patient. After application of the solution to the nail surface, the solvent evaporates and a film/coating is formed on the surface. The film/coating has the capacity to release the antifungal and keratolytic agents in therapeutic levels over a prolonged period of time.

The combination of an antifungal and keratolytic agent is advantageous because it increases the penetration of the antifungal agent through the nail. Because the amount of water in the nail is very low, it is essential to achieve relatively high concentrations of water in the film. The humectant is added to the present invention in order to retain water in the film after the evaporation of the organic solvents. The film formed after evaporation of the volatile solvents contains the pharmaceutically effective agents, polymers, humectant, the water entrapped by the humectant, and additional non-volatile excipients. The presence of water in the film is of significant importance because it maintains the active agents in a saturated-reservoir solution, thus enabling the solubilized agents to be released in a controlled manner into the nail.

The combination of glycerol (humectant), water and low concentrations of keratolytic and antifungal agents, used in the present invention, are particularly advantageous. The water entrapped in the film by the glycerol hydrates the nail and enables low concentrations of the keratolytic agent to be used in order to increase the permeability of the nail. Consequently lower concentrations of the antifungal agent will be adequate in order to diffuse through the nail and provide the desired pharmacological action. Such a combination would reduce the unwanted side effects caused by high keratolytic agent and antifungal agent concentrations. An additional advantage of the use of low keratolytic agent and antifungal agent concentrations is the reduction of the product price.

The antifungal agents are preferably amphothericin B, butefanine, butoconazole, carbol-fuchsin, ciclopirox, clioquinol, clotrimazole, econazole, gentian violet, ketoconazole, miconazole, naftifine, nystatin, oxiconazole, sodium thiosulfate, terbinafine, terconazole, tolnaftate, undecylenic acid, therapeutically acceptable salts thereof, derivatives thereof, and mixtures thereof, more preferably clotrimazole and miconazole nitrate, most preferably miconazole nitrate. Preferably the concentration of the antifungal agents in the varnish solution is less than about 1% (w/w) and most preferably 0.3–0.9% (w/w).

Preferably the concentration of the antifungal agents based on the weight of the non-volatile components is less than about 5% (w/w) and most preferably 0.3–4.7% (w/w).

The keratolytic agents are added to the present invention in order to increase the permeability of and penetration into the nail.

The keratolytic agents are preferably urea, sulfur, salicylic acid, podophyllum resin, and mixtures thereof, most preferably urea. Preferably the concentration of the keratolytic agents in the varnish solution is less than about 1% (w/w), and most preferably 0.3–0.9% (w/w). Preferably the concentration of the keratolytic agent based on the weight of the non-volatile components is in the range from about 0.05% to about 5% (w/w).

The antibacterial agents are preferably bacitracin, clindamycin, erythromycin, gentamicin, mupirocin, neomycin, tetracyclines, polymyxin B, benzalkonium chloride, boric acid, hexachlorophene, iodine, iodoquinol, mafenide, mercury ammoniated, metronidazole, nitrofurazone, selenium sulfide, silver sulfadiazine, salts thereof, derivatives thereof, and mixtures thereof Preferably the concentration of the antibacterial agents in the varnish solution is in the range from about 0.01% to about 1% (w/w), and most preferably 0.2–0.8% (w/w). Preferably the concentration of the antibacterial agents based on the weight of the non-volatile components is in the range from about 0.05% to about 5% (w/w) and most preferably 1.5–4.5% (w/w).

The antiviral agents are preferably acyclovir, amantadine, cidofovir, famciclovir, foscarnet, ganciclovir, palivizumab, penciclovir, ribavirin, rimantadine, valcyclovir, salts thereof, derivatives thereof, and mixtures thereof. Preferably the concentration of the antiviral agents in the varnish solution is in the range from about 0.08% to about 0.8% (w/w) and most preferably 0.2–0.6% (w/w). Preferably the concentration of the antiviral agents based on the weight of the non-volatile components is in the range from about 0.8% to about 8% (w/w) and most preferably 2–6% (w/w).

The antipsoriatic agents are preferably alclometasone, amcinonide, betamethasone, clobetasol, clocortolone, desonide, desoximetasone, diflorasone, fluocinolone, fluocinonide, flurandrenolide, halcinonide, hydrocortisone, mometasone, prednicarbate, triamcinolone, salts thereof, derivetives thereof, and mixtures thereof. Preferably the concentration of the antipsoriatic agents in the varnish solution is in the range from about 0.02% to about 2% (w/w) and most preferably 0.2–1.5% (w/w). Preferably the concentration of the antipsoriatic agents based on the weight of the non-volatile components is in the range from about 0.1% to about 10% (w/w) and most preferably 1–7.5% (w/w).

Since the water content of the nail is very low it is important to achieve relatively high concentrations of water in the delivery system. The humectant is added to the varnish solution in order to hold the water in the film after evaporation of the organic solvents. The presence of water in the film hydrates the nail so that the active agents can be delivered into the deeper layers of the nail. The humectant is preferably glycerol, sorbitol, and mixtures thereof, most preferably glycerol. Preferably the concentration of the humectant in the varnish solution is in the range from about 3% to about 15% (w/w), and most preferably 4–10% (w/w).

Preferably the concentration of the humectant based on the weight of the non-volatile components is in the range from about 5% to about 35% (w/w), and most preferably 10–30% (w/w).

Although glycerol can serve at lower concentrations (less than 2% w/w based on the total weight of the composition) as a plasticizer, at this lower concentration range glycerol is not efficient as a humectant and therefore higher concentrations (above 3% w/w) of glycerol are required in order to be effective as a humectant.

Preferably the water concentration in the varnish solution is less than about 5% (w/w), more preferably 0.5–4.5% (w/w) and most preferably 1–4.5% (w/w). Preferably the concentration of the water in the film is in the range from about 0.4% to about 25% (w/w), more preferably 0.8–20% (w/w), and most preferably 2–18% (w/w).

The delayed release polymeric film-forming agents are preferably hydrophobic (water insoluble) polymers. The hydrophobic (water insoluble) polymers are preferably hydrophobic cellulose derivatives, hydrophobic methacrylic polymers, cellulose acetate phthalate, shellac, derivatives thereof and mixtures thereof. The hydrophobic cellulose derivatives are preferably ethyl cellulose of any acceptable molecular weight.

The hydrophobic methacrylic polymers are preferably methacrylic acid copolymer type B (USP/NF), methacrylic acid copolymer type C (USP/NF), ammonio methacrylate copolymer type B (USP/NF) and ammonio methacrylate copolymer type A (USP/NF), derivatives thereof, and mixtures thereof. The hydrophobic methacrylic polymers are preferably Eudragit S, Eudragit L, Eudragit RS, and Eudragit RL manufactured by Rohm Pharma, but hydrophobic methacrylic polymers from other sources can also be used. The polymers provide a uniform film, retard the release rate of the drugs (agents), and can be mixed in regulated amounts to attain the desired drug release characteristics.

Preferably the concentration of the polymeric film-forming agent in the varnish solution is less than about 7.5% (w/w). Preferably the concentration of the polymeric film-forming agent based on the total weight of the non-volatile components is in the range from about 8% to about 35% (w/w), more preferably 18–30% (w/w) and most preferably 23–27% (w/w).

Preferably the weight ratio of polymer to the antifungal agent is in the range from about 1:0.01 to about 1:0.3 and most preferably is in the range from about 1:0.06 to about 1:0.25.

Preferably the weight ratio of polymer to the keratolytic agent is in the range from about 1:0.01 to about 1:1 and most preferably is in the range from about 1:0.05 to about 1:1.

Preferably the weight ratio of polymer to antibacterial agent is in the range from about 1:0.01 to about 1:0.3 and most preferably is in the range from about 1:0.05 to about 1:0.25.

Preferably the weight ratio of polymer to antiviral agent is in the range from about 1:0.02 to about 1:0.2 and most preferably is in the range from about 1:0.05 to about 1:0.2.

Preferably the weight ratio of polymer to antipsoriatic agent is in the range from about 1:0.006 to about 1:0.15, and most preferably is in the range from about 1:0.01 to about 1:0.15.

Plasticizers are added to the varnish solution in order to enhance the plasticity of the film formed and to modify the sustained release characteristics of the polymer. The plasticizer is preferably dibutyl sebacate, diethyl phthalate, lanolin alcohols, mineral oil, petrolatum, polyethylene glycol, propylene glycol, triacetin, triethyl citrate, or mixtures thereof, and most preferably polyethylene glycol with molecular weight of 300–6000.

Preferably the concentration of the plasticizer in the varnish solution is in the range from about 0.1% to about 2% (w/w), more preferably 0.2–1% (w/w), and most preferably 0.4–0.8% (w/w). Preferably the concentration of the plasticizer based on the total weight of the non-volatile components is in the range from about 0.5% to about 10% (w/w), more preferably 1–5% (w/w), and most preferably 2–3% (w/w).

Preferably, the weight ratio of the plasticizer to the polymer is in the range from about 0.04:1 to about 0.3:1, and most preferably, the weight ratio of the plasticizer to polymer is in the range from about 0.05:1 to about 0.2:1.

Preferably the volatile solvent is selected from the group consisting of an alcohol, a ketone, and mixtures thereof The alcohol is preferably ethanol, isopropyl alcohol, methanol and mixtures thereof The ketone is preferably acetone.

Preferably the volatile solvent is a mixture of acetone and isopropyl alcohol.

Preferably the volatile solvent is present in an amount of from about 60% to about 90% (w/w), and most preferably from about 70% to about 85% (w/w) relative to the total weight of the composition.

Preferably the volumetric ratio of acetone to isopropyl alcohol is in the range from about 1:4 to about 4:1 and most preferably from about 1:3 to about 3:1.

Preferably the solvent system further includes at least one non-volatile solvent. The at least one non-volatile solvent is preferably benzyl alcohol, benzyl benzoate, corn oil, cottonseed oil, ethyl oleate, glycerin, glycofural, isopropyl myristate, isopropyl palmitate, mineral oil, peanut oil, polyethylene glycol, propylene glycol, propylene carbonate, sesame oil, soybean oil, water, and mixtures thereof. .

Optional ingredients include at least one additive chosen from among the group consisting of preservatives, antioxidants, surfactants and coloring agents which are well known in the art.

The preservative is preferably benzoic acid, benzyl alcohol, bronopol, butyl paraben, chlorbutanol, chlorocresol, cresol, ethyl paraben, methyl paraben, phenol, propyl paraben, sodium benzoate, sodium propionate, sorbic acid, or mixtures thereof The antioxidant is preferably alpha tocopherol, ascorbic acid, ascorbyl palmitate, butylated hydroxyanisole, butylated hydroxytoluene, ftimaric acid, malic acid, propyl gallate, sodium ascorbate, sodium metabisulfite, or mixtures thereof.

The surfactant is preferably cetrimide, sodium lauryl sulfate, docusate sodium, glyceryl monooleate, polysorbates, sorbitan esters, or mixtures thereof The coloring agent is preferably amaranth, brilliant blue, caratenoids, carmoisine, curcumin, eosine, erythrosine, fluorescein, rhodoxantin, tetrazine, or mixtures thereof.

The composition prepared according to the present invention may advantageously be presented in the form of varnish or spray.

For a better understanding of the object of the invention, several examples of this composition are described; these are intended as purely illustrative examples without any intention of being limiting. It is to be understood that the invention is not limited in its application to the details of construction and the arrangement of the components set forth in the following description. The invention includes other embodiments and can be practiced or implemented in various ways. It is also to be understood that the phraseology and terminology employed herein is for the purpose of description only and should not be regarded as limiting.

EXAMPLES OF THE FORMULATIONS OF THE PRESENT INVENTION

EXAMPLE 1

The formulations of the present invention were all prepared according to the general procedure which is described below (Preparation of Varnish).

Antifungal Nail Varnish Sustained Release Formulations
(Quantities are in % (w/w))

| Formulation No | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Urea | 0.7 | 0.7 | 0.7 | 0.7 | 0.8 | 0.8 | 0.8 | 0.7 | 0.7 | 0.7 | 0.7 | 0.7 | 0.9 | 0.9 | 0.8 |
| Clotrimazole | | | | | | | | | | | 0.9 | 0.8 | 0.4 | 0.9 | 0.8 |
| Miconazole nitrate | 0.8 | 0.8 | 0.8 | 0.8 | 0.8 | 0.8 | 0.9 | 0.8 | 0.98 | 0.4 | | | | | |
| Ethyl Cellulose | | | 0.8 | 0.8 | 3.4 | 4.2 | 4.3 | | | | | | | | |
| Eudragit S | 7.3 | 6.5 | 6.2 | 5.0 | | | | | 7.3 | 7.4 | 7.3 | 7.3 | 7.4 | 7.3 | 7.3 |
| Eudragit RS | | | | | | | 0.9 | 7.3 | | | | | | | |
| Water | 4.0 | 4.1 | 4.1 | 4.1 | 4.3 | 4.2 | 4.4 | 4.1 | 4.1 | 4.1 | 4.0 | 4.0 | 4.0 | 4.1 | 4.1 |
| Acetone | 61.3 | 61.8 | 61.5 | 62.3 | 63.9 | 63.3 | 65.6 | 61.3 | 61.2 | 61.5 | 61.2 | 61.2 | 61.5 | 61.0 | 61.1 |
| Isopropyl alcohol | 20.4 | 20.6 | 20.5 | 20.8 | 21.3 | 21.1 | 21.8 | 20.4 | 20.4 | 20.5 | 20.4 | 20.4 | 20.5 | 20.3 | 20.4 |
| PEG 400 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 |
| Glycerol | 4.9 | 5.0 | 4.9 | 5.0 | 5.1 | 5.1 | 5.2 | 4.9 | 4.9 | 4.9 | 4.9 | 4.9 | 4.9 | 4.9 | 4.9 |

General Procedure for the Varnish Preparation

A mixture of acetone and isopropyl alcohol was prepared. Water was added to the organic mixture and then urea was dissolved in the solution. PEG and the antifungal agent (miconazole nitrate) were added and dissolved in the solution. When the antifungal agent was completely dissolved, the humectant was added to the solution. Thereafter the polymer was added to the solution. The solution was brought to the final weight using the organic mixture prepared in the first step. All the steps of the varnish preparation were performed while continuously stirring the solution.

Film Preparation

The films were cast from the varnish solutions onto glass surfaces (petri dishes). The solvent was allowed to evaporate for 24 h and the film was removed from the surface. Films of 100×104 cm in thickness were prepared and used for testing of (1) water residue in the film (2) dissolution rate of the active agents from the film and (3) sustained antifungal activity in vitro.

EXAMPLE 2

Determination of the Water Residue in the Films

All the films were tested using the Karl Fisher method to determine the water content.

| Formulation No.* | Water in dry film, % (w/w) |
|---|---|
| 1 | 12 |
| 1** | 5 |
| 6 | 13 |
| 6** | 4 |
| 7 | 13 |
| 7** | 3 |

*The formulation No. is related to the table in Example 1
**without glycerol

These results show that the humectant is able to hold the water in the dry film.

EXAMPLE 3

Dissolution Rates of the Active Agents (Miconazole Nitrate and Urea)

Films were cut to a circular form, 2.54 cm² in area, and were weighed accurately. Film thickness was measured with a micrometer. The membranes were attached to a specially designed dissolution basket in which only one surface of the membrane was exposed to the dissolution medium. 150 ml of 1% sodium lauryl sulfate solution served as the dissolution medium. The dissolution rates were measured in a Van-Kel (VK 7000) dissolution test apparatus at 32° C. and 100 rpm rotating speed.

Aliquots were withdrawn at various times and replaced by fresh solvent, with corrections being applied in the calculations. The amount of drug released was determined spectrophotometrically at 230 nm for miconazole and 564 nm (color reaction) for urea.

The dissolution rates of miconazole nitrate and urea are presented in the is following tables:

Dolution Rates of Miconazole Nitrate From the Formulations Described in Example 1

| | Amount drug released (%) | | | | |
|---|---|---|---|---|---|
| Formulation | 60 min | 120 min | 240 min | 489 min | 1440 min |
| 1 | 7.5 | 21.2 | 37.8 | 50.2 | 96.1 |
| 6 | 6.5 | 11.8 | 20.8 | 30.5 | 61.2 |
| 7 | 5.1 | 8.4 | 14.2 | 20.6 | 52.4 |
| 14 | 7.0 | 16.0 | 21.8 | 28.9 | 70.1 |

Dissolution Rates of Urea From the Formulations Described in Example 1

| | Amount drug released (%) | | | | |
|---|---|---|---|---|---|
| Formulation | 60 min | 120 min | 240 min | 480 min | 1440 min |
| 1 | 15.8 | 33.4 | 59.7 | 96.2 | |
| 6 | 10.2 | 26.1 | 42.5 | 65.0 | 99.8 |
| 7 | 8.6 | 19.1 | 38.9 | 49.2 | 95.1 |
| 14 | 11.2 | 24.0 | 46.2 | 61.0 | 98.6 |

The results show that both miconazole nitrate and urea are released from the films in a controlled manner. The release of urea is higher than miconazole nitrate, this can be explained by the higher solubility and lower molecular weight of urea, compared to miconazole nitrate. The faster release of urea compared to miconazole nitrate is advantageous since higher concentrations of urea increases the permeability of the nail thereby enabling better penetration of the antifungal agent (miconazole) into deeper layers of the nail.

EXAMPLE 4

Sustained Release Activity of Clotrimazole and Miconazole Nitrate In Vitro

A strain of *Saccharomyces cerevisiea* was used in this study. A 1:10 dilution of a stock suspension of the above organism was mixed with mycological culture medium and poured into petri dishes. 5 mm diameter discs of the film (Formulation No 1, 6, 7, 14) containing clotrimazole or miconazole nitrate were placed on the hardened medium and incubated for 24 h at 30° C. Thereafter the films were transferred to another set of petri dishes containing the same medium plus *Saccharomyces cerevisiea*.

Inhibition zones were recorded after incubation period of 24 hours. All samples were tested in triplicate. The mean inhibition zone sizes are summarized in the following table. Inhibition Zones of *S. cerevisiea* Growth by Sustained Release Films Containing Miconazole Nitrate (Formulation No 1.6,7) and Clotrimazole (Formulation No 14).

| Time | Inhibition Zone (mm) Formulation No | | | |
|---|---|---|---|---|
| | 1 | 6 | 7 | 14 |
| 24 hrs | 30.67 | 28.77 | 28.37 | 28.64 |
| 48 hrs | 24.29 | 20.60 | 24.95 | 25.83 |
| 72 hrs | 21.57 | 21.72 | 24.03 | 21.39 |
| 96 hrs | 20.59 | 21.09 | 24.28 | 21.11 |
| 144 hrs | 18.18 | 19.52 | 22.94 | 20.01 |

The measurements of the inhibition zone were discontinued after 6 days. There was no inhibition of Saccharomyces growth in control samples of the film containing no antifungal agent. The results reveal that the antifungal agent embedded in the film is pharmacologically active and is able to inhibit the growth of *Saccharomyces cerevisiea* strain for a prolonged period of time.

Examples of Using the Formulations

The compositions of the present invention may be applied to the infected nail and surrounding tissues once a day up to once a week.

It is understood that the precise concentrations and duration of treatment is a function of the tissue being treated. It is to be noted that concentrations may also vary with the age and condition of the individual treated. It is to be further understood that for any particular subject, the frequency of application should be adjusted over time according to the individual need and professional judgment of the physician or person administering or supervising the administration of the formulations.

It will be appreciated that the above descriptions are intended only to serve as examples, and that many other embodiments are possible within the spirit and the scope of the present invention.

What is claimed is:

1. A sustained release therapeutic nail varnish composition comprising:
   (a) an antifungal effective amount of an antifungal agent;
   (b) a keratolytic agent in an amount sufficient to increase and facilitate penetration of said antifungal agent into the nail;
   (c) greater than 3% (w/w) of a humectant to trap water;
   (d) water in an amount sufficient to hydrate the nail and thereby to further increase permeability of the nail in combination with said keratolytic agent;
   (e) a liquid nail lacquer component comprising a polymeric film forming agent and a volatile solvent, said agent selected to form a sustained release film upon application of said composition on a nail and evaporation of said volatile solvent; said sustained release film configured to trap water from said composition and maintain it in contact with said nail, said water and said humectant in combination still further facilitating penetration of said antifungal agent into the nail, and thereby enhancing therapeutic effectiveness of said antifungal agent.

2. The nail varnish of claim 1, wherein said antifungal agent is selected from the group consisting of amphothericin B, butefanine, butoconazole, carbol-fuchsin, ciclopirox, clioquinol, clotrimazole, econazole, gentian violet, ketoconazole, miconazole, naftifine, nystatin, oxiconazole, sodium thiosulfate, terbinafine, terconazole, tolnaftate, undecylenic acid, therapeutically acceptable salts thereof, derivatives thereof and mixtures thereof.

3. The nail varnish of claim 2, wherein said antifungal agent is clotrimazole or miconazole nitrate.

4. The nail varnish of claim 1, wherein said keratolytic agent is selected from the group consisting of urea, sulfur, salicyclic acid, podophyllum resin and mixtures thereof.

5. The nail varnish of claim 1, wherein said keratolytic agent is urea.

6. The nail varnish of claim 1, further comprising an antibacterial agent, an antiviral agent, an antipsoriatic agent or mixtures thereof.

7. The nail vanish of claim 6, wherein said antibacterial agent is selected from the group consisting of bacitracin, clindamycin, crythromycin, gentamicin, mupirocin, neomycin, tetracyclines, polymyxin B, benzalkonium chloride, boric acid, hexachlorophene, iodine, iodoquinol, mafenide, mercury ammoniated, metronidazole, nitrofurazone, selenium sulfide, silver sulfadiazine, salts thereof, derivatives thereof and mixtures thereof.

8. The nail varnish of claim 6, wherein said antiviral agent is selected from group consisting of acyclovir, amantadine, cidofovir, famciclovir, foscarnet, ganciclovir, palivizumab, penciclovir, ribavirin, rimantadine, valcyclovir, salts thereof, derivatives thereof, and mixtures thereof.

9. The nail varnish of claim 6, wherein said antipsoriatic agent is selected from the group consisting of alclometasone, amcinonide, betamethasone, clobetasol, clocortolone, desonide, desoximetasone, diflorasone, fluocinolone, fluocinonide, flurandrenolide, halcinonide, hydrocortisone, mometasone, prednicarbate and triamcinolone, salts thereof, derivatives thereof, and mixtures thereof.

10. The nail varnish of claim 1, wherein said humectant is selected from the group consisting of glycerol, sorbitol and mixtures thereof.

11. The nail varnish of claim 1, wherein said water is present in an amount of less than about 5% of the total weight of the composition.

12. The nail varnish of claim 1, wherein said water is present in an amount of from about 0.4% to about 25% of the total weight of the composition excluding said volatile solvent.

13. The nail varnish of claim 1, wherein said polymeric film forming agent is selected from the group consisting of hydrophobic polymers.

14. The nail varnish of claim 13, wherein said hydrophobic polymer is selected from the group consisting of hydrophobic cellulose derivatives, hydrophobic methacrylic polymers, cellulose acetate phthalate, shellac, derivatives thereof, and mixtures thereof.

15. The nail varnish of claim 14, wherein said hydrophobic cellulose derivative is ethyl cellulose.

16. The nail varnish of claim 14, wherein said hydrophobic methacrylic polymer is selected from the group consisting of metacrylic acid copolymer type B (USP/NF), methacrylic acid copolymer type C (USP/NF), ammonio methacrylate copolymer type B (USP/NF) and ammonio methacrylate copolymer type A (USP/NF), derivatives thereof, and mixtures thereof.

17. The nail varnish of claim 1, wherein said polymeric film forming agent is present in an amount of from about 8% to about 35% total weight of the composition excluding said volatile solvent.

18. The nail varnish of claim 1, wherein said polymeric film-forming agent present in a weight ratio of polymer to antifungal agent from about 1:0.01 to about 1:0.3.

19. The nail varnish of claim 1, wherein said polymeric film-forming agent is present in a weight ratio of polymer to keratolytic agent from about 1:0.01 to about 1:1.

20. The nail varnish of claim 6, wherein said polymeric film-forming agent is present in a weight ratio of polymer to antibacterial agent from about 1:0.01 to about 1:0.3.

21. The nail varnish of claim 6, wherein said polymeric film-forming agent is present in a weight ratio of polymer to antiviral agent from about 1:0.02 to about 1:0.2.

22. The nail varnish of claim 6, wherein said polymeric film-forming agent is present in a weight ratio of polymer to antipsoriatic agent from about 1:0.006 to about 1:0.15.

23. The nail varnish of claim 1, further comprising a plasticizer.

24. The nail varnish of claim 23, wherein said plasticizer is selected from the group consisting of dibutyl sebacate, diethyl phthalate, lanolin alcohols, mineral oil, petrolatum, polyethylene glycol, propylene glycol, triacetin, triethyl citrate, and mixtures thereof.

25. The nail varnish of claim 1, wherein said volatile solvent is selected from the group consisting of an alcohol, a ketone, and mixtures thereof.

26. The nail varnish of claim 25, wherein said alcohol is selected from the group consisting of ethanol, isopropyl alcohol, methanol and mixtures thereof, and further wherein said ketone is acetone.

27. The nail varnish of claim 1, wherein said volatile solvent is a mixture of acetone and isopropyl alcohol.

28. The nail varnish of claim 1, wherein said volatile solvent is present in an amount of from about 60% to about 90% of the total weight of the composition.

29. The nail varnish of claim 27, wherein said acetone and said isopropyl alcohol are present in a volumetric ratio of acetone to isopropyl alcohol from about 1:4 to about 4:1.

30. The nail varnish of claim 1, wherein said solvent system further includes at least one non-volatile solvent selected from the group consisting of benzyl alcohol, benzyl benzoate, corn oil, cottonseed oil, ethyl oleare, glycerin, glycofural, isopropyl myristate, isopropyl palmitate, mineral oil, peanut oil, polyethylene glycol, propylene glycol, propylene carbonate, sesame oil, soybean oil, water, and mixtures thereof.

31. A method of preparing a sustained release therapeutic varnish formulation, comprising the steps of:
(a) preparing a solution comprising water and a volatile solvent;
(b) adding water to the solution prepared in (a);
(c) dissolving a keratolytic agent and an antifungal agent into the solution prepared in (b);
(d) adding an humectant to the solution prepared in (c); and
(e) dissolving a polymeric film forming agent in the solution prepared in (d);
said film forming agent being selected so as to form a sustained release film upon application of the formulation on a nail and evaporation of said volatile solvent, said sustained release film configured to trap water in contact with the nail and the surrounding tissues.

32. The sustained release therapeutic nail varnish composition of claim 1 further comprising an excipient.

33. A sustained release therapeutic nail varnish composition comprising:
(a) an antifungal effective amount of an antifungal agent;
(b) a keratolytic agent in an amount sufficient to increase and facilitate penetration of said antifungal agent into the nail;
(c) a humectant to trap water;
(d) a liquid nail lacquer component comprising a polymeric film forming agent and a volatile solvent; and
(e) water;
wherein upon application on a nail, the volatile solvent evaporates and a sustained release film coating forms on the surface of the nail, the sustained release film coating releasing the antifungal and keratolytic agents in respective effective amounts over a prolonged period of time and trapping water in contact with the nail; the humectant retaining water in the film; and said humectant and said water further increasing permeability of the nail surface and still further facilitating penetration of the released antifungal agent below the nail surface.

34. The sustained release therapeutic nail varnish composition of claim 33 further comprising an excipient.

35. A method of treating a fungal infection comprising administering to a subject a therapeutically effective amount of a sustained release therapeutic nail varnish composition, wherein the composition comprises:
(a) an antifungal amount of an antifungal agent;
(b) a keratolytic agent in an amount sufficient to increase and facilitate penetration of said antifungal agent into the nail;
(c) greater than 3% (w/w) of a humectant to trap water in a film;
(d) water in an amount sufficient to hydrate the nail and thereby to increase permeability of the nail in combination with said keratolytic agent;
(e) a liquid nail lacquer component comprising a polymeric film forming agent and a volatile solvent;
said film forming agent being selected so as to form a sustained release film upon application of said composition on a nail of said subject and evaporation of said volatile solvent, said sustained release film configured to trap water from said composition and maintain it in contact with said nail, said water and said humecant in combination facilitating penetration of said antifungal agent into the nail, and thereby enhancing effectiveness of said antifungal agent.

36. The method of claim 31 said formulation being suitable application by spraying.

37. A sustained release therapeutic nail varnish composition comprising:
(a) an antifungal effective amount of an antifungal agent;
(b) a keratolytic agent in an amount sufficient to increase and facilitate penetration of said antifungal agent into the nail;
(c) greater than 3% (w/w) of a humectant to trap water;

(d) water in an amount sufficient to hydrate the nail and thereby to finer increase permeability of the nail in combination with said keratolytic agent;

(e) a liquid nail lacquer component comprising a polymeric film forming agent and a volatile solvent, said agent selected to form a sustained release film upon application of said composition on a nail afflicted with a fungal infection and evaporation of said volatile solvent, said film delivering to said nail water, antifungal agent and keratolytic agent from said composition over a prolonged period of time, said water and humectant agent further facilitating penetration of said antifungal agent into the nail and thereby enhancing effectiveness of said antifungal agent.

38. The nail varnish of claim 1, wherein said antifungal agent is present in an amount of less than about 1% of the total weight of the composition.

39. The nail varnish of claim 1, wherein said keratolytic agent is present in an amount of less than about 1% of the total weight of the composition.

* * * * *